United States Patent
Foley et al.

(10) Patent No.: US 11,434,216 B2
(45) Date of Patent: Sep. 6, 2022

(54) PREPARATION OF 3-HYDROXY-3,6-DIMETHYLHEXAHYDROBENZOFURAN-2-ONE AND DERIVATIVES THEREOF

(71) Applicant: P2 SCIENCE, INC., Woodbridge, CT (US)

(72) Inventors: Patrick Foley, New Haven, CT (US); Yonghua Yang, Niantic, CT (US); Tania Salam, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 17/231,877

(22) Filed: Apr. 15, 2021

(65) Prior Publication Data

US 2021/0230132 A1    Jul. 29, 2021

Related U.S. Application Data

(60) Continuation of application No. 16/458,981, filed on Jul. 1, 2019, now Pat. No. 11,008,299, which is a division of application No. 15/759,135, filed as application No. PCT/US2016/051334 on Sep. 12, 2016, now Pat. No. 10,399,954.

(60) Provisional application No. 62/259,269, filed on Nov. 24, 2015, provisional application No. 62/217,094, filed on Sep. 11, 2015.

(51) Int. Cl.
| | | |
|---|---|---|
| *C07D 307/83* | (2006.01) | |
| *A61Q 13/00* | (2006.01) | |
| *C07C 45/66* | (2006.01) | |
| *A23L 27/00* | (2016.01) | |
| *A23L 27/20* | (2016.01) | |
| *A61K 8/49* | (2006.01) | |

(52) U.S. Cl.
CPC ........ *C07D 307/83* (2013.01); *A23L 27/2052* (2016.08); *A23L 27/88* (2016.08); *A61K 8/4973* (2013.01); *A61Q 13/00* (2013.01); *C07C 45/66* (2013.01); *A23V 2002/00* (2013.01); *C07C 2601/16* (2017.05)

(58) Field of Classification Search
CPC .... C07D 307/83; A61K 8/4973; A61Q 13/00; A23L 27/88; A23L 27/2052; C07C 45/66; C07C 2601/16; A23V 2002/00
See application file for complete search history.

(56) References Cited

U.S. PATENT DOCUMENTS

| | | | |
|---|---|---|---|
| 5,464,824 A | 11/1995 | Gaudin | |
| 6,512,126 B2 | 1/2003 | Koch et al. | |

FOREIGN PATENT DOCUMENTS

| | | |
|---|---|---|
| CN | 102850309 | 8/2014 |
| JP | H07-503281 A | 4/1995 |
| JP | 2004-512331 A | 4/2004 |
| WO | WO 2017/044957 | 3/2017 |

OTHER PUBLICATIONS

Chavan, et al., "A Short and Efficient Synthesis of (-) Mintlactone and (+) iso-Mintlactone*," *Tetrahedron Letters*, vol. 49, No. 29, pp. 6429-6436, (1993).

Effenberger, et al., "Enzyme Catalyzed Addition of Hydrocyanic Acid to Substituted Pivalaldehydes—A Novel Synthesis of (R)-Pantolactone," *Tetrahedron: Asymmetry*; vol. 6, No. 1, pp. 271-282 (1995).

Gao, et al., "Expeditious Construction of (+)-Mintlactone via Intramolecular Hetero-Pauson—Khand Reaction," *Journal of Organic Chemistry*, vol. 74, No. 6, pp. 2592, (2009).

Gaudin, J.-M., "Synthesis and Organoleptic Properties of p-Menthane Lactones," *Tetrahedron Letters*, vol. 56, No. 27, pp. 4769-4776, (2000).

Shishido, et al., "An Efficient Total Synthesis of (-)-Mintlactone and (+)-Isomintlactone," *Tetrahedron Letters*, vol. 33, pp. 4589-4592, (1992).

*Primary Examiner* — Timothy R Rozof
(74) *Attorney, Agent, or Firm* — Hoxie & Associates LLC

(57) ABSTRACT

The present invention relates to the synthesis of intermediate compounds which can be used in the synthesis of mint lactone and related compounds, including 3,6-dimethyl-hexahydrobenzofuran-2-ones, isomers, and other derivatives.

9 Claims, No Drawings

PREPARATION OF 3-HYDROXY-3,6-DIMETHYLHEXAHYDROBENZOFURAN-2-ONE AND DERIVATIVES THEREOF

CROSS-REFERENCE TO RELATED APPLICATIONS

This application is a continuation application of U.S. application Ser. No. 16/458,981, filed on Jul. 1, 2019, which is a divisional application of U.S. application Ser. No. 15/759,135, filed on Mar. 9, 2018, which is a U.S. National Stage application of International Application No. PCT/US2016/051334 filed on Sep. 12, 2016, which claims priority benefit under 35 U.S.C. § 119(e) of U.S. Provisional Patent Application No. 62/217,094, filed on Sep. 11, 2015, and U.S. Provisional Patent Application No. 62/259,269, filed on Nov. 24, 2015. The entire disclosures of each of the aforementioned patent applications are incorporated by reference in their entireties.

FIELD OF THE INVENTION

The present invention relates generally to a process for preparing mint lactone from 3-hydroxy-3,6-dimethylhexahydrobenzofuran-2-one. More particularly, the present invention relates to a process for preparing 3-hydroxy-3,6-dimethylhexahydrobenzofuran-2-one from isopulegol and derivatizing 3-hydroxy-3,6-dimethylhexahydrobenzofuran-2-one to produce new and existing organoleptic compounds.

BACKGROUND OF THE INVENTION

Generally, mint lactone is a natural component of mint oil, and a potential precursor to 3,6-dimethylhexahydrobenzofuran-2-one, a valued flavor and fragrance ingredient. Multiple efforts have been made to cost effectively produce mint lactone, which include the hydrogenation and elimination of hydroxymenthofurolactone (I), which comprises the formula:

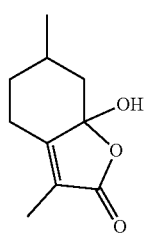

(I)

as described in Koch (U.S. Pat. No. 6,512,126), and the treatment of 3-methylcyclohexanone (II), which comprises the formula:

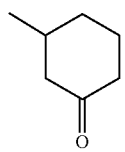

(II)

Compound (II) is treated with methyl pyruvate in a multi-step synthesis involving sodium borohydride and iron chloride as described in Xiong (CN 102,850,309). While both of these approaches are practicable, they use relatively expensive starting materials and reagents (e.g., Pd/C, NaBH$_4$). Another major drawback to these methods is that these methods do not produce highly enantio-enriched material. Additional approaches, including the use of citronellal (Shishido, et al., TetrahedronLetters, 33(32), 4589-4592 (1992)), and alkynyl aldehydes (Gao et al., Journal of Organic Chemistry, 74(6), 2592 (2009)), have also been described, but again lack economic feasibility.

Through use of naturally occurring and commercially available isopulegol (III), a key precursor (IV) in the synthesis of mint lactone (V), can be easily obtained that allows the desired natural stereochemistry to be retained all while using inexpensive and commercially available reagents as shown in the following equation, Scheme A:

Scheme A

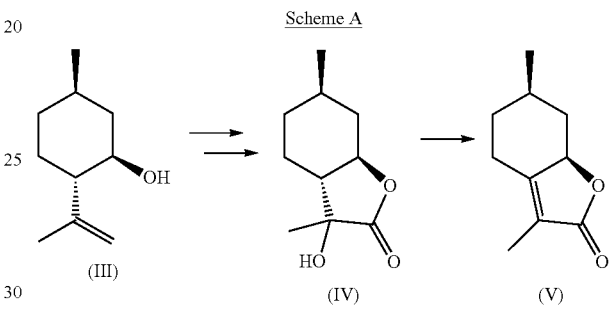

Although isopulegol (III) has been used as a starting material for the synthesis of enantiopure mint lactone in the past (Chavan et al., TetrahedronLetters, 49(29), 6429-6436 (1993)), the approaches appear to have the common problem of being too costly to be commercially attractive, including the use of hydroboration and deprotonation with lithium diisopropyl amide under cryogenic conditions.

As a result of the limitations of these previous approaches, mint lactone and several related materials, such as 3,6-dimethylhexahydrobenzofuran-2-one (also known as Koumalactone®) have been very expensive to obtain commercially, especially with the desired stereochemistry, and therefore their use has been limited.

Additionally, specific isomers of mint lactone's saturated analogs can be difficult to obtain using traditional routes (Gaudin, TetrahedronLetters 56(27), 4769-4776 (2000); Gaudin (U.S. Pat. No. 5,464,824)). In this regard, the invention described herein addresses these problems. Particularly, through certain aspects of this invention, compound (IV) can be deoxygenated to generate the desired isomers directly in a facile, high yielding manner.

In view of the disadvantages inherent in the known types of methods now present in the prior art, the present invention provides an improved method to produce mint lactone, derivatives thereof, and related materials.

SUMMARY OF THE INVENTION

The following discloses a simplified summary of the specification in order to provide a basic understanding of some aspects of the specification. This summary is not an extensive overview of the specification. It is intended to neither identify key or critical elements of the specification nor delineate the scope of the specification. Its sole purpose is to disclose some concepts of the specification in a simplified form as to prelude to the more detailed description that is disclosed later.

Described herein are compounds, compositions, and methods of generating the compounds thereof, some of which could be useful as a flavor and fragrance ingredient.

According to one aspect of the present invention, a method of synthesizing mint lactone (V) is provided, in which isopulegol (III) can be treated with $O_3$ to cleave the double bond, followed by quenching with sodium bisulfite—or any suitable quenching agent—to remove peroxide and generate 1-(2-hydroxy-4-methyl-cyclohexyl)ethanone (VI). It is noted that the terms "quenching," "quench," or "quenched" as used herein mean decomposing a reactive species in order to stop a reaction and to convert intermediate products to stable materials which can be isolated or removed. This hydroxyl ketone (VI) can then be treated with a solution of aqueous sodium cyanide or potassium cyanide, optionally in the presence of ammonium chloride, to generate a cyanohydrin intermediate that can be hydrolyzed in the presence of a strong aqueous acid, for example concentrated hydrochloric acid, to generate a-hydroxylactone (IV). Other stereoisomers of isopulegol can be used as well to generate the corresponding versions of compound (IV). All downstream chemistries can also be contemplated with stereoisomers of isopulegol. An example of the reaction can be illustrated by the following equation, Scheme B:

Scheme B

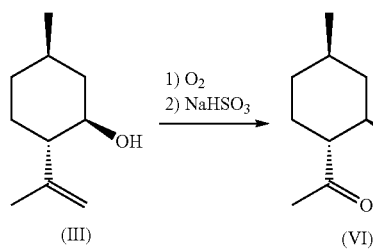

(III) → 1) $O_2$ 2) $NaHSO_3$ → (VI) → 1) $NaCN/NH_4Cl$ 2) HCl →

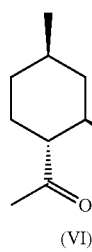

(IV)

Compound (IV) can then be treated with known conditions to eliminate the alcohol to generate enantiopure mint lactone (Shishido et al., *TetrahedronLetters*, 33(32), 4589-4592 (1992)), and subsequently reduced to generate enantio-enriched 3,6-dimethylhexahydrobenzofuran-2-one. Compound (IV) can also be deoxygenated (e.g., through halogenation and reduction) to generate enantio-enriched 3,6-dimethylhexahydrobenzofuran-2-ones. Thus, compound of formula (IV) represents a valuable intermediate for preparing mint lactone.

In another embodiment, compound (IV) can also be derivatized through esterification or alkylation to make new organoleptic compounds, some of which are described herein.

In another embodiment, mint lactone (V) can also be treated with base under catalytic hydrogenation conditions to generate desirable mixtures of isomers. In particular, treatment of mint lactone (V) with base under hydrogenation conditions generates desired isomers (VII) and (VIII), but also yields desired isomers (IX) and (X), which add very desirable olfactory properties to the mixture.

In this regard, the present invention provides isomers having the following formula:

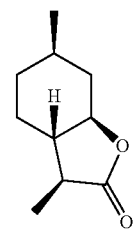

(VII)

and/or a compound of formula (VIII)

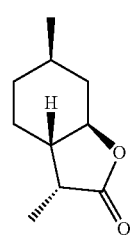

(VIII)

and/or a compound of formula (IX)

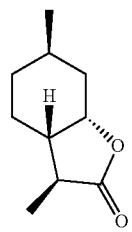

(IX)

and/or a compound of formula (X)

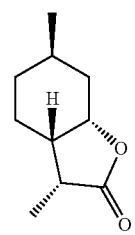

(X)

In another embodiment, compound (IV) can be derivatized at the hydroxyl position to generate new organoleptic compounds (XI)

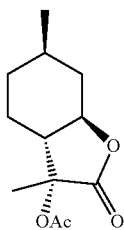

(XI)

and (XII).

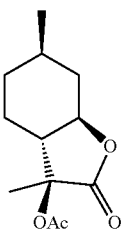

(XII)

In this regard, compounds (XI) and (XII) are derived from 3-hydroxy-3,6-dimethylhexahydrobenzofuran-2-one. Compounds (XI) and (XII) comprise a delicate, sweet and creamy odor that is reminiscent of coconut and butter. Thus, compounds (XI) and (XII) are used in fragrance and flavoring formulation.

In certain embodiments, compound (IV) is halogenated to provide compound (XIII):

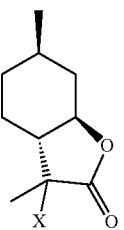

(XIII)

wherein, X is a halogen. This halide intermediate (XIII) can be dehalogenated to provide compounds (VII) and (VIII).

DETAILED DESCRIPTION OF THE INVENTION

The present invention is directed towards an industrially applicable, economical and advantageous process for the preparation of mint lactone, derivatives thereof, and, related materials. Various modifications obvious to one skilled in the art are deemed to be within the spirit and scope of the present invention.

The word "exemplary" is used herein to mean serving as an example, instance, or illustration. Any aspect or design described herein as "exemplary" is not necessarily to be construed as preferred or advantageous over other aspects or designs. Rather, use of the word exemplary is intended to disclose concepts in a concrete fashion. As used in this application, the term "or" is intended to mean an inclusive "or" rather than an exclusive "or." The articles "a" and "an" as used in this application and the appended claims should generally be construed to mean "one or more" or "at least one" unless specified otherwise or clear from context to be directed to a singular form. Additionally, the terms "formula," "compound," and "structure" are used interchangeably unless the context clearly indicates otherwise.

The ozonolysis of isopulegol (III) to obtain hydroxy-ketone (VI) is a known reaction, which can be done in the presence of water in good yield. Surprisingly, however, this β-hydroxy ketone does not readily eliminate to the corresponding enone when treated with a cyanide salt such as NaCN or KCN in the presence of ammonium chloride. Rather, this ketone forms a cyanohydrin in good yield at ambient temperature and pressure. Also surprisingly, when in the presence of ammonium chloride, no amino acid forms as one might expect given the likeness to Strecker-type conditions (Strecker, *Annalen der Chemie and Pharmazie*, 91(3), 349-351 (1854)). Further, this cyanohydrin can be readily hydrolyzed in the presence of aqueous acid, at which point a seemingly simultaneous intramolecular lactonization occurs to yield compound (IV) as a mixture of stereoisomers with regard to the a-hydroxy position. It is noted that a phase transfer catalyst is used to facilitate reaction with a non-aqueous phase during the cyanohydrin formation.

Without wishing to be bound by theory, the reaction proceeds through the cyanide addition to compound (VI) to generate an intermediate described by structure (XIV) shown in the equation below. This nitrile (XIV) is then hydrolyzed to the corresponding acid, which may or may not undergo simultaneous intramolecular lactonization to desired compound (IV). This pathway is depicted in the following equation, Scheme C:

Scheme C

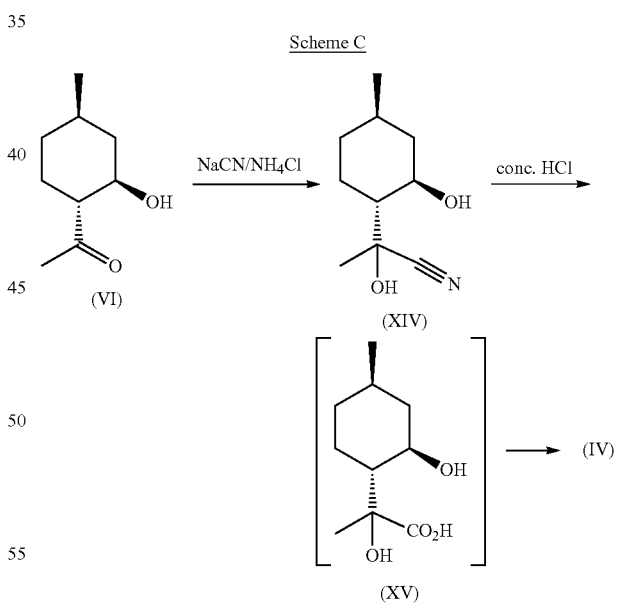

This inventive, nitrile-assisted homologation and lactonization allows for the known hydroxy-ketone to be converted to compound (IV) using inexpensive reagents such as sodium cyanide, potassium cyanide, ammonium chloride, and hydrochloric acid. Once obtained, compound (IV) can be dehydrated through elimination using reagents such as tosyl chloride, mesyl chloride, thionyl chloride, or phosphorous oxychloride in the presence of a base, such as pyridine, to afford mint lactone (V). Other elimination techniques such as heat, strong acid (e.g., $H_2SO_4$, HBr, HCl, HI), and radical assisted deoxygenation can also be employed.

Additionally, compound (V) can be reduced to 3,6-dimethylhexahydrobenzofuran-2-one using any number of enone reduction techniques, such as hydrogenation in the presence of a catalyst (e.g., Pd, Ru, Ni, Rh, Cu, etc.) hydride reduction using hydride reducing agent (e.g., lithium aluminum hydride, sodium borohydride, diisopropyl aluminum hydride, sodium bis(2-methoxyethoxy)aluminumhydride available under the trade name Red-Al®) or enzymatic reduction. It is noted that the term "hydrogenation" as used herein means a reduction reaction wherein hydrogen is the reducing agent.

It should be noted that hydrogenation in the presence of base can unexpectedly offer a desirable mixture of isomers that cannot be easily obtained through hydrogenation in the absence of base. Specifically, base treatment, such as treatment with sodium methoxide or sodium hydroxide can result in hydrogenation from the more hindered face of compound (V) to result in compounds (VII)

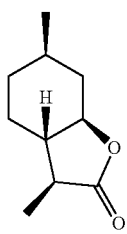

(VII)

and (VIII),

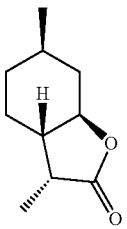

(VIII)

perhaps through a "ring-opened" intermediate. Unexpectedly, however, the treatment with base allows some product to be inverted at the hydroxyl carbon position—so called carbon 7a—to result in compound (IX)

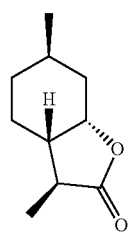

(IX)

and compound (X) as well,

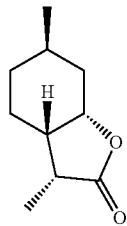

(X)

which add a powerful creamy or lactonic quality to the mixture.

Additionally, following compounds having formula (XVI)

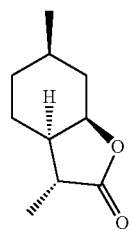

(XVI)

and (XVII) are formed.

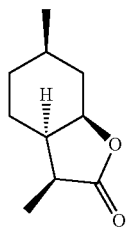

(XVII)

Table 1 below shows percentages of isometric mixture of 3,6-dimethylhexahydrobenzofuran-2-one where Condition A is the hydrogenation of compound (V) in the presence of Raney Nickel at room temperature using methanol as a solvent; and Base Treatment is stirring compound (V) in methanol in the presence of 4.0 eq of sodium methoxide at room temperature for two hours in advance of hydrogenation.

TABLE 1

| Compound | VII | VIII | IX | X | XVI | XVII | Comments |
|---|---|---|---|---|---|---|---|
| Condition A with Base Treatment | 17.5% | 1.2% | 7.4% | 13.6% | 47% | 6.4% | Powerful lactonic character |
| Condition A without Base Treatment | 0% | 0% | 0% | 6.4% | 1.4% | 87.6% | Weak coumarinic/ lactonic character |

Compound (IV) can also be directly deoxygenated, thereby allowing for the retention of desired stereochemistry as in compounds (VII) and (VIII). For example, compound (IV) can be halogenated using a reagent such as thionyl chloride, PCl$_3$, POLI$_3$, HCl, cyanuric chloride, PCl$_5$, SO$_2$Cl$_2$, CCI$_4$, PBr$_3$, HBr, HI, or any other suitable halogenating agent. The term "halogenating agent" as used herein means a compound capable of substituting hydrogen atom of an aromatic ring system by halogen atom. The halide intermediate can then be reduced using catalytic hydrogenation in the presence of a catalyst (e.g., Pd, Ru, Ni, Rh, Cu) through electrolysis, or through treatment with Zn in a suitable acid, such as acetic acid. These transformations can be carried out stepwise, or in tandem, as shown in Scheme D.

Scheme D

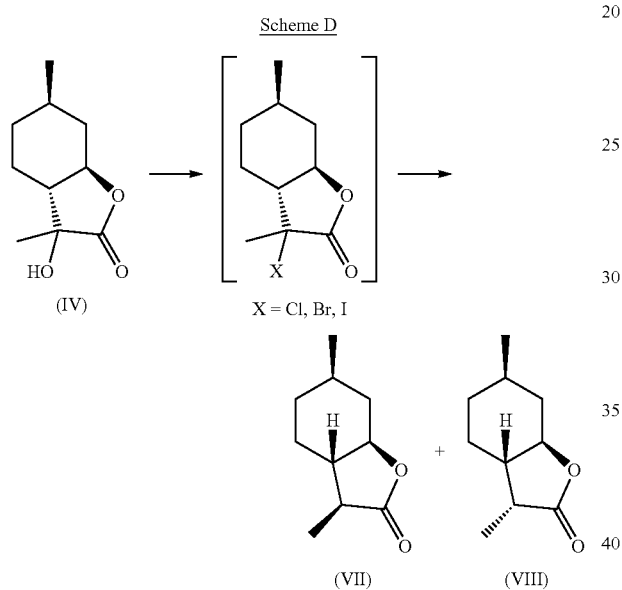

A preferred embodiment of this invention involves the chlorination of Compound (IV) to generate compound (XVIII) using SOQ2, or PCl3, and then treating the chlorinated product with Zn in acetic acid at elevated temperature (70-100° C.) to yield compounds (VII) and (VIII) in high yield and purity. It should be noted that compounds (VII) and (VIII) are highly sought after fragrance materials that possess a very powerful lactonic and coumarinic type odor. This reaction is shown in Scheme E, below.

Scheme E

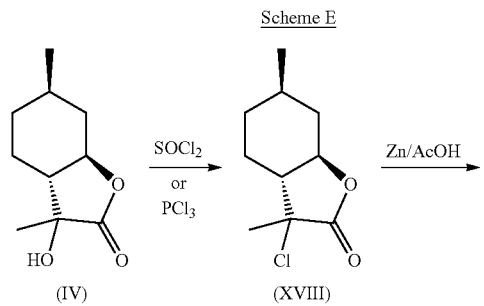

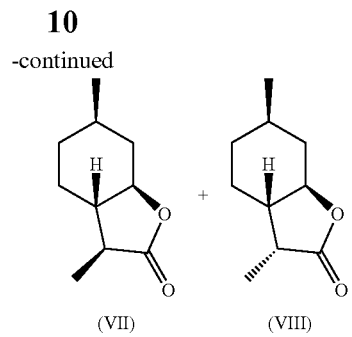

Compound (IV) can further be derivatized at the hydroxyl position to generate new organoleptic compounds. For example, compound (IV) can be acetylated to yield compounds (XI) and (XII) depicted below in Scheme F. The mixture of these products has a delicate, sweet and creamy odor that is reminiscent of coconut and butter. It is contemplated that other esters and ethers can also be made that will likely have desirable properties as well.

Scheme F

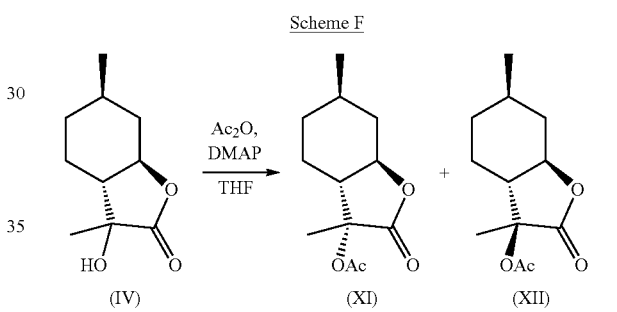

Finally, it was observed that the major byproduct formed during the hydro-cyanation and the subsequent hydrolysis was the chiral enone, (XIX), also known as (R)-1-(4-methylcyclohex-1-en-1-yl)ethanone.

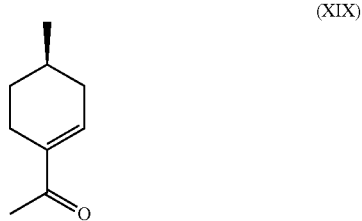

Given the purity of this co-product and its potential utility as a chiral synthetic intermediate, its production directly from compound (VI) was investigated. It was found that excellent conversions and purity could be obtained by treating compound (VI) with acid, such as Amberlyst®, and dehydrating compound (VI) at an elevated temperature. This pathway is depicted in Scheme G, below.

Scheme G

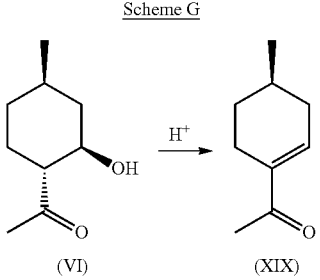

EXPERIMENTAL

Example 1

Synthesis of Compound (VI) from Compound (III)

Isopulegol (150 g, 0.97 mmol) was combined with H$_2$O (300 mL) and the mixture was cooled to 10° C. in a jacketed glass reactor equipped with an overhead stirrer and gas diffuser. An O 3/O 2 mixture was bubbled through the reaction for 5 hours making sure the reaction did not exceed 15° C. Following complete consumption of starting material, 121 g of NaHSO$_3$ was added at 0° C. and was allowed to warm to room temperature overnight. The aqueous phase was then extracted with MTBE (350 mL×2), washed with Na$_2$CO$_3$ (10% aqueous), and then dried with Na$_2$SO$_4$, filtered, and concentrated.

This resulted in 138.7 g of white crystalline solid, 91.3% of theoretical yield, with an estimated purity of 97.9%. H NMR (CDCl$_3$, 500 MHz), δ 0.87 (d, J=6.5 Hz, 3H, —CH$_3$), 0.86-0.96 (m, 2H, —CH$_2$—), 1.16-1.25 (m, 1H, —CH$_2$—), 1.37-1.44 (m, 1H, —CH$_3$), 1.62-1.67 (m, 1H, —CH$_2$—), 1.84-1.91 (m, 2H, —CH$_2$—), 2.10 (s, 3H, —CH$_3$), 2.22-2.27 (m, 1H, —CH—), 3.00 (s, broad, 1H, —OH), 3.71-3.76 (m, 1H, —CHO—).

Example 2

Synthesis of Compound (IV) from Compound (VI)

31.2 g (20 mmol) of hydroxy-ketone II, methyl t-butyl ether (100 mL), tetrabutylammonium hydrogensulfate (0.1 g), and saturated aqueous NH$_4$Cl (150 mL) were placed into a 500 mL three-necked round-bottom flask equipped with a thermometer and a 250 mL addition funnel. The apparatus was assembled in a well-ventilated hood and the flask was surrounded by an ice-bath. A solution of NaCN (19.8 g, 40 mmol) in water (100 mL) was added drop wise through the addition funnel, making sure the temperature was kept under 15° C. The reaction was kept stirring for another 2 hours at this condition. Methyl t-butyl ether (100 mL) and water (100 mL) were added to the reaction mixture, and the mixture was transferred into a separation funnel and the aqueous layer was removed.

The organic layer was again washed with water (100 mL). The organic layer was then evaporated to yield the crude product as a clear oil. The product was then treated with HCl (35%) at 80° C. to 90° C. for 2 hours. The reaction was then quenched with H$_2$O (150 mL) and neutralized to pH=5 to 6 with aqueous N a$_2$c c)$_3$ (10%). Methyl t-butyl ether was used to extract the aqueous mixture (250 mL×2), and the combined organic layers were dried with anhydrous Na$_2$SO$_4$, filtered, and evaporated to remove all solvent. The resulting semi-solid was triturated with heptane (50 mL) and white powder formed immediately.

The liquid phase was decanted and the solid was washed with heptane (50 mL) again. The solid was dried under vacuum pressure for 1 hour to give the product 22.2 g as a white solid. The aqueous phase was treated with ferrous sulfate and kept separately as the waste. 1H-NMR and $^{13}$C-NMR showed there were two isomers as the ratio of ~1:4, which can be separated further through column chromatograph (Silica gel, EtO Ac/Heptane).

Major isomer: H NMR (CDCl$_3$, 500 MHz), δ 0.92 (d, J=6.5 Hz, 3H, —C¾), 0.95-1.01 (m, 1H, —CH$_2$—), 1.12-1.22 (m, 2H, —CH$_2$—), 1.22 (s, 3H, —C¾), 1.46-1.54 (m, 1H, —CH$_2$—), 1.71-1.74 (m, 1H, —CH$_2$—), 1.77-1.82 (m, 1H, —CH$_2$—), 1.84-1.89 (m, 1H, —CH—), 2.1 1-2.15 (m, 1H, —CH—), 3.72 (td, J=11 Hz, J=4.0 Hz, 1H, —CHO—), 3.81 (s, broad, 1H, —OH). $^{13}$C NMR (125 MHz, CDCl$_3$) δ 17.5, 21.6, 22.1, 30.9, 33.5, 38.5, 53.4, 74.6, 79.5, 180.3.

Example 3

Synthesis of Compound (V) from Compound (IV)

3.7 g (2 mmol) of hydroxylactone, and pyridine (10 mL) were place into a 250 mL three-necked round-bottom flask equipped with a water condenser. Tosyl chloride (5.7 g, 3 mmol) was slowly added as a solid with good stirring. The reaction was then heated to 120° C. for 10 hours. The reaction was then cooled down to room temperature and water was added (100 mL), followed by HCl (IN) until the pH=5 to 6. Methyl t-butyl ether (100 mL×2) was used to extract the mixture. The combined organic phases were then dried with anhydrous sodium sulfate, filtered, and evaporated to yield a red liquid as the crude product. Following chromatography purification (silica gel, EtOAc/Heptane: 5 to 25%), 2 g of product was obtained as a liquid. H NMR (CDCl$_3$, 500 MHz), δ 0.90-1.06 (m, 5H, —CH$_3$, —CH$_2$—), 1.65-1.74 (m, 1H, —C¾—), 1.79-1.80 (m, 3H, —CH$_3$), 1.91-1.95 (m, 1H, —CH$_2$—), 2.18 (td, J=14 Hz, J=5.5 Hz, 1H, —CH$_2$—), 2.38-2.43 (m, 1H, —CH$_2$—), 2.78 (dt, J=14 Hz, J=2.5 Hz, 1H, —CH—), 4.60 (dd, J=11 Hz, J=6.0 Hz, 1H, —CHO—).

Example 4

Synthesis of Compounds (VII) and (VIII) from Compound (IV)

Step 1: Synthesis of Compound (XVIII) from Compound (IV)

Compound (IV) (36.8 g, 0.2 mol) was dissolved in THF (500 ml) at room temperature in a round-bottomed flask and was then treated with SOCl$_2$ (47.6 g, 0.4 mol). The reaction was then brought to reflux. After 20 minutes, 20 ml of pyridine was added slowly to the reaction. The reaction was monitored by GC and TLC for approximately 3 hours until all of the starting material was consumed. The reaction was then cooled to room temperature and water was slowly added until phase separation occurred. The organic phase was removed and the aqueous phase was extracted twice with 200 ml of MTBE. The organic phases were then combined and treated with aqueous base until the aqueous phase had a pH of 8.

After phase separation, the organic phase was dried with Na$_2$SO$_4$, filtered and concentrated to give solid that could then be triturated with heptane (3×100 ml) to give 22.0 g of compound (XVI) as an off-white solid as the major isomer with H NMR as follows: H NMR (CDCl$_3$, 500 MHz), δ 1.00-1.12(m, 4H, —CH$_2$—, —CH$_3$), 1.18-1.25(m, 1H, —CH$_2$—), 1.49-1.72 (m, 6H, —CH$_2$—, —CH$_3$), 1.72-1.87 (m, 2H, —CH$_2$—), 2.24-2.27 (m, 1H, —CH—), 4.11-4.18 (m, 1H, —CHO—). $^{13}$C NMR (125 MHz, CDCl$_3$) δ 21.9, 22.9, 23.8, 31.0, 33.4, 37.8, 55.5, 65.6, 80.2, 173.9.

Step 2: Synthesis of Compounds (VII) and (VIII) from Compound (XVIII)

Compound (XVI) (22.0 g, 108.5 mmol) was dissolved in acetic acid (62 ml) and was brought to 80° C. in a round-bottomed flask with magnetic stirring. Zinc powder (14 g, 217 mmol) was slowly added to the solution. The reaction was stirred for two hours until GC and TLC showed complete consumption of starting material. The reaction was then cooled to room temperature, diluted with water (200 ml), and extracted with MTBE (2×150 ml). The combined organic phases were treated with 10% by wt. aqueous Na$_2$CO$_3$ until the aqueous phase was basic. The organic phase was separated, dried with Na$_2$SO$_4$, filtered and concentrated to give 18.8 g of crude solid. This solid was then crystallized and filtered using cold heptane, resulting in 9.0 g of white crystals of (VII) as the major isomer and (VIII) as the minor isomer.

The major isomer (~95%) was obtained with H NMR as follows: H NMR (CDCl$_3$, 500 MHz), δ 0.97-1.15(m, 4H, —CH—, —CH$_3$), 1.13-1.27(m, 5H, —CH$_2$—, —CH$_3$), 1.39-1.47 (m, 1H, —CH$_2$—), 1.56-1.63 (m, 1H, —CH$_2$—), 1.76-1.79 (m, 1H, —CH$_2$—), 1.88-.191(m, 1H, —CH—), 2.17-2.25(m, 2H, —CH$_2$—), 3.69-3.75(m, 1H, —CHO—). $^{13}$C NMR (125 MHz, CDCl$_3$) δ 12.4, 21.9, 26.6, 31.3, 34.1, 38.2, 41.3, 51.4, 82.3, 179.3.

Example 5

Synthesis of Compounds (XI) and (XII) from Compound (IV)

Compound (IV) (5 g, 27 mmol) was combined with N,N-dimethylaminopyridine (DMAP) (0.33 g, 2.7 mmol) and 100 mL of tetrahydrofuran (THF) in a round bottom flask placed in an ice bath equipped with a magnetic stirrer and rubber septum. Acetic anhydride (4.2 mL, 44 mmol) was added drop wise using a syringe. When the reaction was complete by GC FID analysis, 0.8 mL of H$_2$O was added to quench any remaining anhydride, and then an additional 10 mL H$_2$O was added. The THF was then removed from the mixture using a rotary evaporator, and the 10% aqueous Na$_2$CO$_3$ was added until the pH=8. The aqueous mixture was then extracted with ethyl acetate, and the organic layer was dried with anhydrous sodium sulfate, filtered, and concentrated to give 5.9 g of organic residue.

This residue was then purified using silica chromatography. A solvent system of 8 to 15% ethyl acetate in heptane was used as eluent, and the two major products were obtained.

One product was obtained as the major isomer with H NMR as follows: H NMR (CDCl$_3$, 500 MHz), δ 1.01 (d, J=6.5 Hz, 3H, —CH$_3$), 1.01-1.08 (m, 1H, —CH$_2$—), 1.26-1.40 (m, 2H, —CH$_2$—), 1.41 (s, 3H, —CH$_3$), 1.55-1.61 (m, 1H, —CH$_2$—), 1.79-1.88 (m, 2H, —CH$_2$—), 2.08 (s, 3H, —CH$_3$), 2.25 (dt, J=11 Hz, J=1.0 Hz, 1H, —CH—), 2.65-2.70 (m, 1H, —CH—), 3.78 (td, J=11 Hz, J=3.5 Hz, 1H, —CHO—).

Example 6

Synthesis of Compound (XIX) from Compound (VI)

230 g (1.47 mol) of compound (VI) was dissolved in 500 ml of Toluene, charged with 4.6 g of Amberlyst® 15 catalyst, and was placed in a round bottomed flask equipped with a Dean Stark apparatus for removal of water. The mixture was heated at 80-140° C., including all ranges and subranges therebetween, and more preferably, at 110-130° C. for 7 hours until all water had appeared to stop forming. In some embodiments, dehydration was performed continuously. The Amberlyst® was then filtered out and the toluene was removed. The isolated residue was then distilled at around 1.0 mbar and 65-70° C. (42-48° C. head temperature) to obtain 173.2 g of >97% pure desired product, (R)-1-(4-methylcyclohex-1-en-1-yl)ethanone (i.e., compound (XIX)): H NMR (CDCl$_3$, 500 MHz), δ 0.97(d, J=6.5 Hz, 3H, —CH$_3$), 1.13-1.21(m, 1H, —CH$_2$—), 1.61-1.67 (m, 1H, —CH$_2$—), 1.80-1.88 (m, 1H,—CH$_2$—), 2.05-2.14 (m, 1H, —CH$_2$—), 2.27 (s, 3H, —CH$_3$), 2.30-2.45 (m, 2H, —CH$_2$—), 6.85 (m, 1H, —CH=C).

The second, minor isomer was obtained with H NMR as follows: H NMR (CDCl$_3$, 500 MHz), δ 1.02 (d, J=6.5 Hz, 3H, —CH$_3$), 1.00-1.08 (m, 1H, —CH$_2$—), 1.13-1.20 (m, 1H, —CH$_2$—), 1.28-1.36 (m, 1H, —CH$_2$—), 1.61 (s, 3H, —CH$_3$), 1.57-1.63 (m, 2H, —CH$_2$—), 1.82-1.86 (m, 1H, —CH$_2$—), 1.89-1.93 (m, 1H, —CH—), 2.06 (s, 3H, —CH$_3$), 2.24-2.28 (m, 1H, —CH—), 4.13-4.19 (m, 1H, —CHO—).

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A method of producing (R)-1-(4-methylcyclohex-1-en-1-yl)ethanone, having the general formula (XIX):

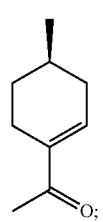

(XIX)

Comprising the steps of:
(a) providing a compound having the general formula (VI):

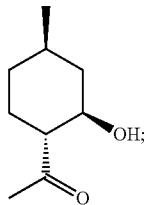

(VI)

and
(b) dehydrating said compound, to produce the compound of Formula (XIX).

2. The method of claim 1, wherein said dehydration is catalyzed by an acid.

3. The method of claim 2, wherein said acid is a cationic resin.

4. The method of claim 2, wherein said dehydration is performed continuously.

5. The method of claim 2, wherein said dehydration is performed at an elevated temperature.

6. The method of claim 5, wherein said temperature is between 80° C. and 140° C.

7. The method of claim 3, wherein said acid is an Amberlyst-type cationic resin.

8. The method of claim 2, wherein said dehydration is carried out in toluene solvent.

9. The method of claim 6, wherein said temperature is between 110° C. and 130° C.

* * * * *